(12) United States Patent
Nakagaki et al.

(10) Patent No.: US 7,527,718 B2
(45) Date of Patent: May 5, 2009

(54) METHOD OF TREATING GAS SENSOR ELEMENT

(75) Inventors: Kunihiko Nakagaki, Nagoya (JP); Sang Jae Lee, Ama-Gun (JP); Hiroyuki Shindo, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 773 days.

(21) Appl. No.: 11/091,349

(22) Filed: Mar. 28, 2005

(65) Prior Publication Data

US 2005/0210657 A1 Sep. 29, 2005

(30) Foreign Application Priority Data

| Mar. 29, 2004 | (JP) | ............................. 2004-095540 |
| Mar. 4, 2005 | (JP) | ............................. 2005-060520 |

(51) Int. Cl.
*G01N 27/26* (2006.01)

(52) U.S. Cl. ........................ 204/426; 204/425; 204/427; 205/784.5; 73/23.31; 73/23.32

(58) Field of Classification Search ......... 204/421–432; 73/1.06, 23.31–23.32; 205/781, 783.5–785
See application file for complete search history.

(56) References Cited

U.S. PATENT DOCUMENTS

| 4,253,934 A | 3/1981 | Berg et al. |
| 4,650,697 A * | 3/1987 | Kitagawa et al. ............ 427/453 |
| 4,655,892 A * | 4/1987 | Satta et al. ............. 204/192.15 |
| 6,156,175 A * | 12/2000 | Kato et al. .................. 204/424 |
| 6,540,884 B1 * | 4/2003 | Siddle et al. ........... 204/192.22 |

FOREIGN PATENT DOCUMENTS

| EP | 1 006 352 | 6/2000 |
| JP | 57-131047 | 8/1982 |
| JP | 03-216546 | 9/1991 |

* cited by examiner

*Primary Examiner*—Kaj K. Olsen
*Assistant Examiner*—Bach T Dinh
(74) *Attorney, Agent, or Firm*—Burr & Brown (57) ABSTRACT

A method of treating a gas sensor element for improving measurement characteristics thereof, including: heating the gas sensor element at a temperature of 600-1000° C. for 3-24 hours in a treatment atmosphere in which an oxygen concentration is regulated to be not higher than 0.2% and in which are included: (A) not lower than 1000 ppm of an adsorptive gas component wherein an adsorptive capable of being adsorbed on the measuring electrode is bound to oxygen; and (B) a combustible gas in an amount that can be substantially stoichiometrically oxidized by oxygen that is generated upon reduction or decomposition of the adsorptive gas component, so that the adsorptive gas component is reduced or decomposed for permitting the adsorptive in the adsorptive gas component to be adsorbed on the measuring electrode, and so that the noble metal material of the measuring electrode is reduced.

5 Claims, 3 Drawing Sheets

METHOD OF TREATING GAS SENSOR ELEMENT

This application is based on Japanese Patent Application Nos. 2004-095540 filed on Mar. 29, 2004, and 2005-060520 filed on Mar. 4, 2005, the contents of which are incorporated hereinto by reference.

BACKGROUND OF THE INVENTION

1. Field of the Invention

The present invention relates to a method of treating a gas sensor element. More particularly, this invention relates to such a method of treating a gas sensor element for improving measuring characteristics of the gas sensor element arranged to measure a gas component having bound oxygen such as NOx, SOx, etc., in a measurement gas.

2. Discussion of Related Art

As a sensing device for measuring NOx, SOx, etc., in combustion gases and exhaust gases of internal combustion engines, there are conventionally used a NOx sensor, a SOx sensor, and the like which include a gas sensor element for measuring a gas component (measurement gas component) having bound oxygen such as NOx or SOx, contained in a gas to be measured (measurement gas). The gas sensor such as the NOx sensor or the SOx sensor has various configurations. As one example, there is known a gas sensor constituted by including a gas sensor element which has an electrochemical cell provided by forming, on a solid electrolyte, a measuring electrode capable of reducing or decomposing the measurement gas component having the bound oxygen in the measurement gas and formed of a cermet of a noble metal material and a ceramic material.

Figure 1:
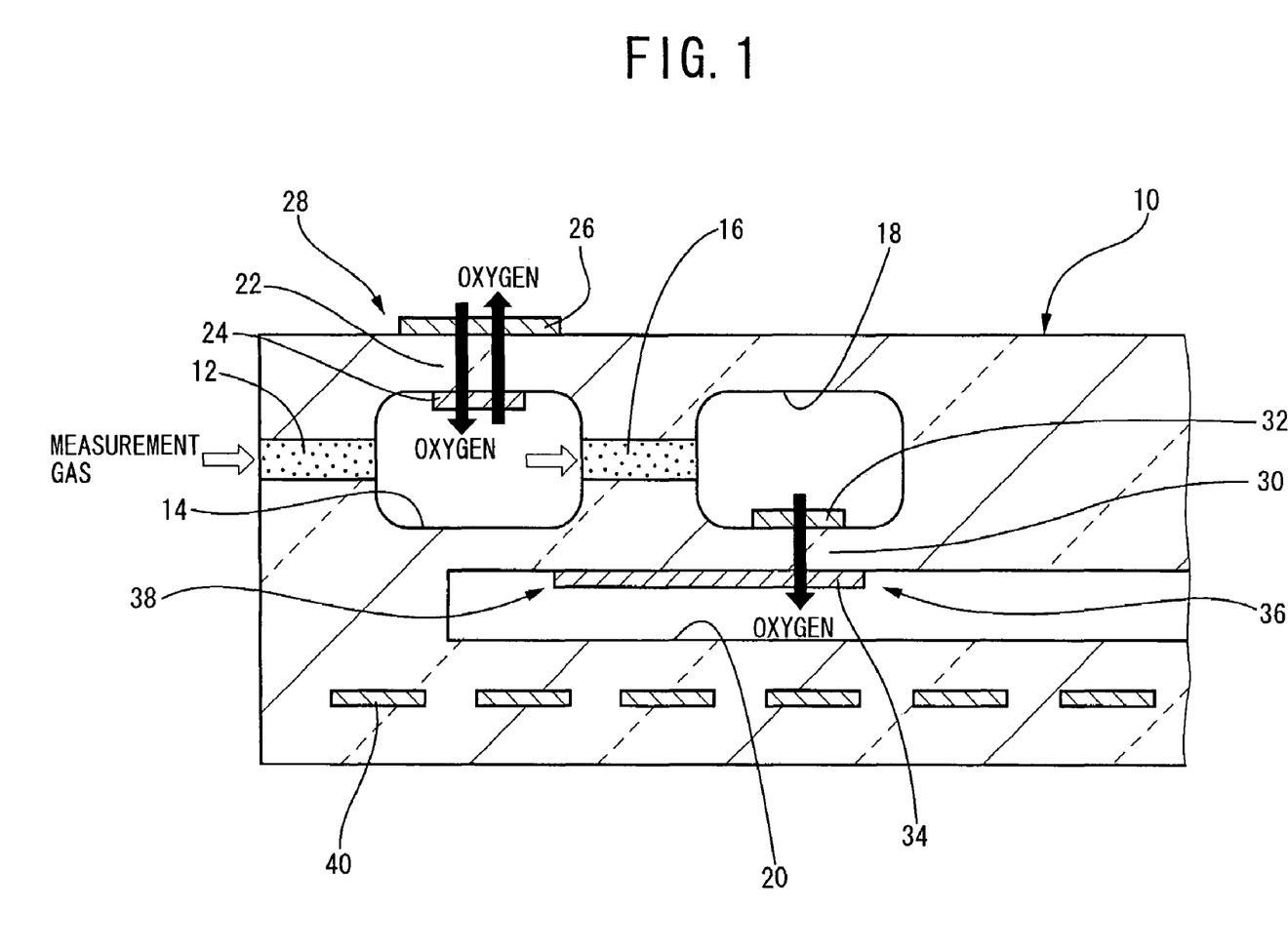
FIG. 1 is a schematic view in cross section showing an internal arrangement of one example of a NOx sensor element.

In such a sensor element of the gas sensor constructed as described above, the NOx sensor, for instance, is constituted by including an oxygen ion-conductive solid electrolyte body 10 such as $ZrO_2$. As shown in FIG. 1 schematically indicating an internal structure of the sensor element, there are formed within the solid electrolyte body 10: a first internal space 14 which is located on a distal side of the solid electrolyte body 10 for communication with an exterior through a first diffusion controlling section 12; a second internal space 18 which communicates with the first internal space 14 through a second diffusion controlling section 16; and a reference-air introducing passage 20 which is open at a proximal end of the solid electrolyte body 10 for communication with an atmospheric air. In the thus constructed sensor element, a measurement gas existing outside the solid electrolyte body 10 is introduced into the first internal space 14 through the first diffusion controlling section 12 under a predetermined diffusion resistance, and an atmosphere (the measurement gas) in the first internal space 14 is introduced into the second internal space 18 through the second diffusion controlling section 16 under a predetermined diffusion resistance, while a reference air is introduced into the reference air-introducing passage 20 through the opening at the proximal end of the solid electrolyte body 10.

In the thus constructed NOx sensor element, a first solid electrolyte portion 22 of the solid electrolyte body 10 in which the first internal space 14 is formed, an inner pumping electrode 24 formed on a portion of the first solid electrolyte portion 22 which is exposed to the internal space 14, and an outer pumping electrode 26 formed on an outer surface portion of the first solid electrolyte portion 22 which is exposed to the exterior of the solid electrolyte body 10 cooperate with one another to constitute an electrochemical cell functioning as a main pumping cell 28. Further, a second solid electrolyte portion 30 interposed between the second internal space 18 and the reference air-introducing passage 20, a measuring electrode 32 formed on a portion of the second solid electrolyte portion 30 which is exposed to the second internal space 18, and a reference electrode 34 formed on a portion of the second solid electrolyte portion 30 which is exposed to the reference air-introducing passage 20 cooperate with one another to constitute an electrochemical cell functioning as a measuring pumping cell 36. Moreover, the first solid electrolyte portion 22, the second solid electrolyte portion 30, the inner pumping electrode 24, and the reference electrode 34 cooperate with one another to constitute an electrochemical pumping cell functioning as an oxygen partial pressure-detecting cell 38. In FIG. 1, a reference numeral 40 indicates a heater for heating the NOx sensor element.

In the NOx sensor element constructed as described above, a desired voltage is applied between the two electrodes 24, 26 of the main pumping cell 28 by using a variable power source (not shown) to allow a current to flow in a predetermined direction, so that oxygen in the atmosphere (the measurement gas) of the first internal space 14 is pumped out into an external measurement gas-existing space, or, on the contrary, oxygen is pumped into the first internal space 14 from the external measurement gas-existing space. An electromotive force induced between the two electrodes 24, 34 of the oxygen partial pressure-detecting cell 38 based on a difference in an oxygen concentration between the atmosphere in the first internal space 14 and the reference air in the reference air-introducing passage 20 is measured by a suitable potentiometer (not shown). Further, a desired voltage is applied between the two electrodes 32, 34 of the measuring pumping cell 36 by using a variable-voltage power source (not shown), so that oxygen in an atmosphere (the measurement gas) of the second internal space 18 is pumped out into the reference air-introducing passage 20. The measuring electrode 32 of the measuring pumping cell 36 is formed of a porous cermet composed of a noble metal material such as rhodium (Rh) capable of reducing or decomposing NOx, and a ceramic material such as zirconia ($ZrO_2$). The measuring electrode 32 functions as a catalyst for reducing or decomposing NOx.

In the NOx sensor element constructed as described above, oxygen is pumped into or out from the first internal space 14 by the oxygen pumping action of the main pumping cell 28, and an oxygen partial pressure in the atmosphere of the first internal space 14 is controlled to be a predetermined, desirably low value that does not allow reduction of NOx, by controlling the voltage of the variable power source to be applied between the two electrodes 24, 26 on the basis of a detected value of oxygen partial pressure in the atmosphere of the first internal space 14 detected by the oxygen partial pressure-detecting cell 38. The atmosphere of the first internal space 14 with the oxygen partial pressure being controlled is introduced into the second internal space 18 via the second diffusion controlling section 16, and NOx in the atmosphere is reduced in the second internal space 18 by the measuring electrode 32 functioning as the catalyst for reducing or decomposing NOx. Oxygen generated upon reduction of NOx is pumped out into the reference air-introducing passage 20 from the second internal space 18 by the oxygen pumping action of the measuring pumping cell 36. In this instance, since the oxygen partial pressure (the oxygen concentration) in the atmosphere of the first internal space 14 is controlled to be constant, a pumping current which is proportional to the concentration of NOx is allowed to flow between the measuring electrode 32 and the reference electrode 34 of the measuring pumping cell 36.

Accordingly, in the conventional NOx sensor element described above, the pumping current in the measuring pumping cell is measured, and the concentration of NOx in the measurement gas is obtained based on the measured pumping current.

For examining detecting sensitivity to the gas of the conventional gas sensor elements having the structure described above, the inventors of the present invention performed various experiments using the NOx sensor element, and it was found that the conventional gas sensor elements suffered from the following problems.

A NOx sensor element which has the structure described above and which is not used yet for measurement after it has been produced was actually installed on a vehicle, and a durability-evaluating test was performed on the NOx sensor element. The result of the test revealed the following: the NOx sensor element suffered from initial deterioration in its NOx detecting sensitivity, that is, the NOx sensor element suffered from about 20%-reduction in the NOx detecting sensitivity at a time point where about 50 hours passed after the moment of initiation of the measurement, and thereafter the detecting sensitivity was stabilized. Further, the concentration of NOx in a measurement gas without containing NOx was measured using the unused NOx sensor element which is not used yet for measurement. Since NOx is not contained in the measurement gas, the pumping current should be zero, and accordingly the NOx concentration should be zero. However, the pumping current of about 0.8 μA was detected, and the NOx concentration corresponding to the detected pumping current was measured. Thus, the NOx sensor element suffered from initial offset in the NOx detecting sensitivity.

Accordingly, it was revealed that, in the conventional gas sensor elements, the initial deterioration and initial offset of the detecting sensitivity to the measurement gas component are inevitably caused, adversely influencing the measurement of the measurement gas component in the measurement gas.

SUMMARY OF THE INVENTION

It is therefore an object of the present invention to provide a technique which eliminates or restrains, in a gas sensor element for measuring a gas component with bound oxygen in a measurement gas, occurrence of the initial deterioration and initial offset of the detecting sensitivity to the gas component in the measurement gas, thereby improving measurement characteristics of the gas sensor element in measuring the gas component included in the measurement gas.

To attain the object indicated above, the inventors of the present invention made various studies on the gas sensor element for measuring the measurement gas component having bound oxygen included in the measurement gas, for examining the cause of occurrence of the initial deterioration and the initial offset of the detecting sensitivity to the measurement gas component. The inventors repeatedly carried out a measuring test for measuring NO in a combustion gas using the unused NOx sensor element which is not used yet after its production, and the following fact was revealed.

During a certain time period after the moment of initiation of measurement of NOx by using the NOx sensor element which is in a unused state, a portion of N (nitrogen) generated when NO is reduced or decomposed on the surface of the measuring electrode in the NOx sensor element is adsorbed on the measuring electrode, and therefore the electrode area active for reduction or decomposition of NO is gradually decreased. This phenomenon of adsorption of N on the surface of the measuring electrode substantially does not occur any more at a certain time point at which the amount of adsorption of N on the measuring electrode reaches a predetermined level.

In forming the measuring electrode composed of the cermet of the noble metal material and the ceramic material, the noble metal material is inevitably oxidized by sintering. Accordingly, when the NOx sensor element in the unused state is initially used for measuring the concentration of NOx, the oxidized noble metal material is reduced as well as NOx, and oxygen generated by reduction of the noble metal is pumped out together with oxygen generated by reduction of NOx. Therefore, at the initial stage of the use of the NOx sensor element, i.e., in the initial period of the measurement, the oxygen generated from the oxidized noble metal material of the measuring electrode is also pumped out when the oxygen generated from NOx is pumped out, so that an excessive amount of the pumping current flows due to the oxygen generated from the noble metal material.

From the fact described above, it is concluded that the initial deterioration of the detecting sensitivity to the gas component experienced in the gas sensor element is caused because a portion of the measurement gas component which is bound to oxygen is adsorbed on the measuring electrode in a limited amount for a certain time period from the moment of initiation of the measurement of the gas component by using the unused gas sensor element to a time point at which a predetermined measuring time has elapsed. It is further concluded that the initial offset of the detecting sensitivity to the gas component is caused because oxygen is generated and emitted from the oxidized noble metal material of the measuring electrode upon reduction thereof at the initial stage of the use of the gas sensor element.

As a result of an extensive study by the inventors based on the conclusions described above, it has been found that the initial deterioration and the initial offset of the detecting sensitivity of the gas sensor element to the measurement gas component can be effectively eliminated or minimized by subjecting the gas sensor element to a heat treatment under predetermined conditions in an atmosphere which includes: a predetermined amount of an adsorptive gas component wherein an adsorptive capable of being adsorbed on the measuring electrode is bound to oxygen; and a predetermined amount of a combustible gas that can be oxidized by oxygen generated upon reduction of the adsorptive gas component.

The present invention has been made based on the findings described above, and the object indicated above may be achieved according to the principle of this invention, which provides a method of treating a gas sensor element for improving measurement characteristics thereof, the gas sensor element including an electrochemical cell provided by forming, on a suitable solid electrolyte, a measuring electrode which is capable of reducing or decomposing a gas component having a bound oxygen in a measurement gas and which is formed of a cermet of a noble metal material and a ceramic material, the gas sensor element being arranged to reduce or decompose the gas component by the measuring electrode and to measure an amount of oxygen generated upon reduction or decomposition of the gas component, for obtaining a concentration of the gas component in the measurement gas, the method comprising: heating the gas sensor element at a temperature of 600-1000° C. for 3-24 hours in a treatment atmosphere in which an oxygen concentration is regulated to be not higher than 0.2% and in which are included: (A) not lower than 1000 ppm of an adsorptive gas component wherein an adsorptive capable of being adsorbed on the measuring electrode is bound to oxygen; and (B) a combustible gas in an amount that can be substantially stoichiometrically oxidized by oxygen that is generated upon reduction or decomposition of the adsorptive gas component, so that the adsorptive gas component is reduced or decomposed for permitting the adsorptive in the adsorptive gas component to be adsorbed on the measuring electrode, and so that the noble metal material of the measuring electrode is reduced.

In the method according to the present invention, before the gas sensor element is used as a gas sensing device for measuring the gas component in the measurement gas, the gas sensor element is subjected to a heat treatment for 3-24 hours at a temperature in a range of 600-1000° C. that substantially corresponds to a state in which the gas sensor element is generally used, in the atmosphere which is in the vicinity of the theoretical air fuel ratio and which includes the adsorptive gas component in a concentration of not lower than 1000 ppm. According to the heat treatment, the adsorptive (element) of the adsorptive gas component is adsorbed on the measuring electrode of the gas sensor element which is not yet used for the measurement of the gas component.

Therefore, by practicing the method according to the invention, an adsorptive which is constituted by an oxygen-bound component in the measurement gas component (i.e., element such as N where the measurement gas component is NO) is prevented, after emission of oxygen therefrom by reduction, from being adsorbed on the measuring electrode of the gas sensor element during the use of the gas sensor element, owing to the adsorptive (element) of the adsorptive gas component which has been adsorbed on the measuring electrode in advance by the heat treatment described above. Accordingly, the amount of adsorption of the adsorptive in the measurement gas component on the measuring electrode can be made zero or can be minimized. Consequently, it is possible to effectively eliminate or restrain that the electrode area active for the reduction of the measurement gas component is gradually decreased by adsorption of the adsorptive in the measurement gas component on the measuring electrode.

In the above-described method of treating a gas sensor element according to the present invention, the oxygen concentration in the treatment atmosphere to which the gas sensor element is exposed during the heat treatment is regulated to be not higher than 0.2% and the combustible gas is included in the treatment atmosphere in an amount that can be substantially stoichiometrically oxidized by oxygen generated upon reduction of the adsorptive gas component. Though oxygen is generated upon reduction of the adsorptive gas component by the heat treatment of the gas sensor element, such oxygen is consumed by oxidization of the combustible gas, so that the reducing capability in the treatment atmosphere can be assured with high stability, whereby the noble metal material of the measuring electrode can be reduced with high reliability by the heat treatment of the gas sensor element. Since the entire amount of the combustible gas can be substantially oxidized, it is avoided that non-oxidized combustible gas component is adsorbed on the measuring electrode to thereby decrease the electrode area active for reduction of the measurement gas component. Therefore, the method of the present invention is effective to prevent reduction of the noble metal material of the measuring electrode and emission of oxygen therefrom at the initial stage of measurement by the gas sensor element.

In a first preferred form of the above-described method of the present invention, the adsorptive gas component is NO, and the NO is included in the treatment atmosphere in a concentration in a range of 3000-7000 ppm.

According to the first preferred form indicated above, by performing the heat treatment in the atmosphere which includes NO as the adsorptive gas component in a concentration held within the specified range, a part of N can be adsorbed on the measuring electrode with higher reliability in a sufficient amount at the time when NO is reduced on the measuring electrode in the gas sensor element. As a result, it is possible to prevent that the initial deterioration in the detecting sensitivity of the gas sensor element to the measurement gas component is caused due to adsorption of the adsorptive in the measurement gas component on the measuring electrode. Hence, the measurement characteristics of the gas sensor element can be advantageously improved.

In a second preferred form of the above-described method of the invention, the oxygen concentration in the treatment atmosphere is in a range of $10^{-8}$-0.1%.

According to the second preferred form indicated above, the oxygen concentration in the treatment atmosphere is kept at a relatively low level, the noble metal material providing the measuring electrode can be reliably reduced. Therefore, it is possible to avoid with higher reliability that the initial offset of the detecting sensitivity to the measurement gas component is caused due to emission of oxygen from the noble metal material by reduction thereof. Thus, the measurement characteristics of the gas sensor element can be more advantageously improved.

In a third preferred form of the above-described method of the invention, the heating the gas sensor element in the treatment atmosphere is carried out at a temperature of 750-900° C. for 4-6 hours.

According to the third preferred form indicated above, the heat treatment of the gas sensor element in the treatment atmosphere can be performed with high efficiency and high reliability, so that the improvement in the measurement characteristics of the gas sensor element can be more effectively attained.

In a fourth preferred form of the above-described method of the invention, the combustible gas is a hydrocarbon gas.

According to the fourth preferred form indicated above, harmless reaction products are obtained by oxidization of the combustible gas. Accordingly, the improvement in the measuring characteristics of the gas sensor element is attained in a safe manner.

BRIEF DESCRIPTION OF THE DRAWINGS

The above and other objects, features, advantages and technical and industrial significance of the present invention will be better understood by reading the following detailed description of a presently preferred embodiment of the invention, when considered in connection with the accompanying drawings, in which.

DETAILED DESCRIPTION OF THE INVENTION

A gas sensor element whose gas measuring characteristics are improved according to the treating method of this invention is adapted for measuring a concentration of a gas component (measuring gas component) having bound oxygen such as NOx or SOx, contained in a gas to be measured (measurement gas) such as a combustion gas or an exhaust gas of an internal combustion engine, and has a known configuration. Such a gas sensor element is used while being installed on various devices with combustion chambers, vehicles such as automotive vehicles, etc. In essence, the treating method of the present invention is applicable to conventionally used NOx sensor elements, SOx sensor elements, and the like.

The gas sensor element to which the method of the present invention is applicable includes an electrochemical cell provided by forming, on a suitable solid electrolyte, a measuring electrode formed of a cermet of a noble metal material and a ceramic material. The noble metal material of the measuring electrode in the electrochemical cell is not particularly limited, but may be suitably selected from among noble metal materials which are conventionally employed for the material of the cermet electrode and which are capable of reducing or decomposing the measurement gas component having bound oxygen such as NOx or SOx, included in the measurement gas. Examples of the noble metal material are Rh, Pd, Pt, an alloy of Rh and Pt, and an alloy of Pt and Pd.

The ceramic material cooperating with the noble metal material to constitute the measuring electrode is not particularly limited, provided that the ceramic material forms a sintered body (cermet) obtained by sintering a composition in which are contained the ceramic material and the noble metal material described above and that the ceramic material is generally used for the material of the cermet electrode. For instance, $ZrO_2$ may be employed as the ceramic material. As the solid electrolyte on which is formed the measuring electrode composed of the constituent material described above, $ZrO_2$ is employed, for instance, which is conventionally used in the gas sensor element, by taking advantage of its property having oxygen ion conductivity.

The gas sensor element constituted by including the electrochemical cell which has the measuring electrode formed of the cermet of the noble metal material and the ceramic material described above, in other words, the gas sensor element whose measurement characteristics can be improved by the method of the present invention has a known configuration arranged to reduce or decompose, by the measuring electrode, the measurement gas component having bound oxygen included in the measurement gas and measure an amount of oxygen generated by reduction or decomposition of the measurement gas component, so as to obtain a concentration of the measurement gas component in the measurement gas.

The operation of the gas sensor element will be explained referring to FIG. 1 showing one example of the NOx sensor element with a known configuration. In such a gas sensor element, for instance, the measurement gas is introduced into the first internal space 14 via the first diffusion controlling section 12, and the oxygen partial pressure of the measurement gas in the first internal space 14 is regulated to a constant value which does not allow the measurement gas component to be reduced, by cooperative action of the main pumping cell 28 and the oxygen partial pressure-detecting cell 38. The measurement gas in the first internal space 14 having the regulated oxygen partial pressure is then introduced, via the second diffusion controlling section 16, into the second internal space 18 where the measurement gas is brought into contact with the measuring electrode 32 formed of the material described above and functioning as a reducing or decomposing catalyst. As a result, the measurement gas component in the measurement gas introduced into the second internal space 18 is reduced or decomposed, and oxygen generated upon reduction of the measurement gas component is pumped out by the measuring pumping cell 36 constituted by including the measuring electrode 32, into the reference air-introducing passage 20, while there is measured a pumping current which flows through the measuring pumping cell 36 depending upon the amount of oxygen pumped out by the measuring pumping cell 36. Thus, on the basis of the measured pumping current, the concentration of the measurement gas component in the measuring gas is obtained.

Like the gas sensor element having the configuration shown in FIG. 1, a gas sensor element configured as described below may be a gas sensor element whose measurement characteristics can be improved according to the method of the present invention. That is, such a gas sensor element includes the main pumping cell 28 and the oxygen partial pressure-detecting cell 38 each of which is constituted by the electrochemical cell. As in the gas sensor element shown in FIG. 1 and explained above, in this gas sensor element, the oxygen partial pressure (oxygen concentration) of the measurement gas introduced into the first internal space 14 is regulated to a constant level by cooperative action of the main pumping cell 28 and the oxygen partial pressure-detecting cell 38, and the measurement gas whose oxygen partial pressure is regulated is introduced into the second internal space 18. In this gas sensor element, however, the measuring pumping cell 36 is replaced with a measuring oxygen partial pressure-detecting cell constituted by an electrochemical cell including the measuring electrode 32, the reference electrode 34, and the second solid electrolyte portion 30. This measuring oxygen partial pressure-detecting cell is arranged to measure an electromotive force generated between the two electrodes 32, 34 thereof based on a difference in oxygen concentration between the measurement gas in the second internal space 18 and the reference air in the reference air-introducing passage 20. Based on the measured electromotive force, the concentration of the measurement gas component in the measurement gas is obtained. The measurement characteristics of the thus arranged gas sensor element can be improved by the treating method of the invention.

In the treating method according to the present invention, the gas sensor element constructed as described above is subjected to the heat treatment in the treatment atmosphere including the predetermined gas components, before the gas sensor element installed or located at a prescribed position where the measurement gas flows is initially used as a sensing device for measuring the gas component having bound oxygen, in the measurement gas, i.e., before the measurement by the gas sensor element is initiated. Owing to the heat treatment, the adsorptive (element) of the adsorptive gas component included in the treatment atmosphere is adsorbed on the measuring electrode while the noble metal material of the measuring electrode is reduced, thereby preventing adsorption, on the measuring electrode, of the prescribed component (element) in the measurement gas which is generated in the initial period of the use of the gas sensor element as the sensing device (i.e., at the initial stage of the measurement of the gas component in the measurement gas), and also preventing reduction of the noble metal material of the measuring electrode. Therefore, the measurement characteristics of the gas sensor element can be improved.

More specifically explained, in the treatment atmosphere to which the gas sensor element is exposed during the heat treatment, the adsorptive gas component is included in which the adsorptive (element) to be adsorbed on the measuring electrode is bound to oxygen. The gas sensor element is subjected to the heat treatment in the treatment atmosphere including the adsorptive gas component, so that the adsorptive gas component is reduced while the adsorptive from which oxygen has been emitted is adsorbed on the measuring electrode. The adsorptive of the adsorptive gas component which is thus adsorbed in advance on the measuring electrode prevents the adsorptive in the measurement gas component from being adsorbed on the measuring electrode after the measurement of the gas component by the gas sensor element is initiated. Therefore, it is possible to effectively eliminate or restrain that the electrode area active for the reduction of the measurement gas component is gradually decreased due to adsorption, on the measuring electrode, of the adsorptive in the measurement gas component. Consequently, the initial deterioration of the detecting sensitivity of the gas sensor element can be advantageously prevented.

While the adsorptive gas component included in the treatment atmosphere is not limited by the kind of the gas component to be measured by the gas sensor element, it is preferable to employ the adsorptive gas component whose adsorptive is the same as the adsorptive in the measurement gas component which might be adsorbed on the measuring electrode at the initial stage of the measurement of the measurement gas component by the gas sensor element. For instance, where the heat treatment is carried on a gas sensor element for measuring a concentration of NOx in the measurement gas, it is preferable to employ, as the adsorptive gas component, NO, $NO_2$ or the like. Where the heat treatment is carried on a gas sensor element for measuring a concentration of SOx in the measurement gas, it is preferable to employ, as the adsorptive gas component, $SO_2$ or the like.

One purpose for carrying out the heat treatment on the gas sensor element in the atmosphere including the adsorptive gas component described above is to prevent the adsorptive in the measuring gas from being adsorbed on the measuring electrode at the initial stage of the use of the gas sensor element which has not been used yet for measuring the measurement gas component, by permitting the adsorptive in the adsorptive gas component to be adsorbed in advance on the measuring electrode of the gas sensor element. Where the adsorptive in the adsorptive gas component is identical with the adsorptive in the measurement gas component, the adsorption power of the adsorptive in the adsorptive gas component at the time of the heat treatment on the unused gas sensor element is the same as that of the adsorptive in the measurement gas component at the initial stage of the use of the gas sensor element. Accordingly, the heat treatment can be performed on the gas sensor element in a state similar to a state in which the measurement of the measurement gas component is carried out by using the gas sensor element, without a need of considering a difference in the adsorption power between the adsorptive in the adsorptive gas component and the adsorptive in the measurement gas component. By thus performing the heat treatment, the adsorptive in the adsorptive gas component can be reliably adsorbed on the measuring electrode as when the adsorptive in the measurement gas component is adsorbed during the measurement of the measurement gas component. Thus, the intended purpose of the heat treatment can be easily attained.

The concentration of the adsorptive gas component in the treatment atmosphere at the time of the heat treatment is not lower than 1000 ppm. If the concentration of the adsorptive gas component is less than 1000 ppm, the amount of adsorption of the adsorptive to be adsorbed on the measuring electrode by the heat treatment on the gas sensor element in the treatment atmosphere is insufficient due to the low concentration of the adsorptive gas component, making it impossible to prevent, to a sufficient extent, the adsorption of the adsorptive in the measurement gas on the measuring electrode at the initial stage of the measurement of the measurement gas component by using the unused gas sensor element. Therefore, the initial deterioration of the detecting sensitivity of the gas sensor element cannot be effectively prevented or restrained.

The upper limit of the concentration of the adsorptive gas component in the treatment atmosphere is suitably determined by taking economy into account without wasting the adsorptive gas component. It is noted that the concentration of the adsorptive gas component in the treatment atmosphere may be suitably changed within the range described above depending upon the kind of the adsorptive gas component to be used. Where the adsorptive gas component is $NO_2$, for instance, the concentration of the adsorptive gas component is preferably not lower than 1000 ppm. Where the adsorptive gas component is NO, for instance, the concentration of the adsorptive gas component is held preferably in a range of 3000-7000 ppm. By suitably changing the concentration of the adsorptive gas component in the treatment atmosphere depending upon the kind thereof, the adsorptive in the adsorptive gas component can be reliably and sufficiently adsorbed on the measuring electrode by the heat treatment performed on the gas sensor element in the treatment atmosphere, and the adsorptive gas component is not wasted, resulting in a cost decrease.

In the treatment atmosphere, the combustible gas is included in addition to the adsorptive gas component. The combustible gas is oxidized by oxygen generated upon reduction of the adsorptive gas component by the heat treatment of the gas sensor element in the treatment atmosphere, and thereby consumes the generated oxygen. Thus, the combustible gas has a function of preventing the reduction capability in the treatment atmosphere from being lowered by inhibiting an increase in the oxygen concentration in the treatment atmosphere which arises from the reduction of the adsorptive gas component.

The kind of the combustible gas is not particularly limited, but may be suitably selected from among those known in the art, provided that the combustible gas can be oxidized at the same time when the adsorptive gas component is reduced. Preferably, a hydrocarbon gas is used as the combustible gas. In particular, it is preferable to use, for instance, methane, propylene, or the like which is comparatively not likely be oxidized at low temperature.

Where the hydrocarbon gas is used as the combustible gas, harmless reaction products such as $CO_2$ and $H_2O$ are generated by the oxidization of the combustible gas. Therefore, the improvement in the measurement characteristics of the gas sensor can be attained in a safe manner. Unlike in a case where a combustible gas which is likely to be easily oxidized at low temperature is used, in a case where methane or propylene which is not likely to be oxidized at low temperature is used, it is possible to prevent that the combustible gas is oxidized, prior to oxidization thereof by the oxygen generated upon reduction of the adsorptive gas component in the treatment atmosphere, by a trace amount of oxygen that is inevitably included in the treatment atmosphere. Therefore, the combustible gas can be oxidized with high reliability by the oxygen generated upon reduction of the adsorptive gas component, thereby preventing the oxygen concentration in the treatment atmosphere from being increased due to the reduction of the adsorptive gas component.

The combustible gas described above needs to be included in the treatment atmosphere in an amount that can be substantially stoichiometrically oxidized by the oxygen generated upon reduction of the adsorptive gas component. Namely, the combustible gas should be included in the treatment atmosphere in such an amount that a substantially entire amount of the combustible gas included in the treatment atmosphere is oxidized by a substantially entire amount of the oxygen generated by reduction of the adsorptive gas component and that the oxygen generated by reduction of the adsorptive gas component and the combustible gas are not present at all or are present in extremely trace amounts, if any, after the oxidization reaction of the combustible gas.

Where the combustible gas is included in the treatment atmosphere in an amount smaller than the amount that can be oxidized by the oxygen generated upon reduction of the adsorptive gas component, the oxygen generated upon reduction of the adsorptive gas component has an increased concentration in the treatment atmosphere during the heat treatment, undesirably deteriorating the reduction capability in the treatment atmosphere. On the other hand, where the combustible gas is included in the treatment atmosphere in an amount larger than the amount that can be oxidized by the oxygen generated upon reduction of the adsorptive gas component, a part of the combustible gas which is not oxidized by such oxygen may be adsorbed on the measuring electrode, and the electrode area of the measuring electrode active for reduction of the measurement gas component may be decreased, causing a risk of deteriorating the detecting sensitivity of the gas sensor element.

The treatment atmosphere in which the combustible gas and the adsorptive gas component are included at respective concentrations described above needs to have an oxygen concentration which is regulated to be not higher than 0.2%. The reason for this is as follows: in the method according to the present invention, the gas sensor element is subjected to the heat treatment in the predetermined treatment atmosphere, whereby the adsorptive in the adsorptive gas component is adsorbed on the measuring electrode while, at the same time, the noble metal material constituting the measuring electrode is reduced. Where the heat treatment on the gas sensor element is performed in the treatment atmosphere in which the oxygen concentration is in excess of 0.2%, the noble metal which is the constituent material of the measuring electrode cannot be sufficiently reduced, making it difficult to prevent occurrence of the initial offset of the measuring sensitivity of the gas sensor element in the initial period of the use thereof.

Described more specifically, since the measuring electrode of the gas sensor element is composed of the cermet of the noble metal material and the ceramic material, the noble metal material is inevitably oxidized upon sintering for forming the measurement electrode composed of the cermet. When the gas sensor element is initially used for measuring the measurement gas after its production with the noble metal material constituting the measuring electrode being kept in the oxidized state, the measuring electrode is heated by contacting the heated measurement gas, and the noble metal material of the measuring electrode is reduced. Oxygen generated when the noble metal material is reduced is pumped out by the oxygen pumping action of the gas sensor element, together with oxygen generated from the measurement gas component in the measurement gas. As a result, the concentration of the measurement gas component to be measured when the unused gas sensor element is initially used is obtained on the basis of a sum of the amount of oxygen generated by reduction of the measurement gas component and the amount of oxygen generated by reduction of the noble metal material. Thus, when the gas sensor element is initially used for measuring the measuring gas after its production, the gas sensor element suffers from the offset in its gas detecting sensitivity in which the concentration of the measurement gas component in the measurement gas to be measured by the gas sensor element is higher than actual concentration.

In view of the above, in the present method, the gas sensor element is subjected, prior to its use, to the heat treatment for reducing the noble metal material constituting the measuring electrode, in order to avoid the adverse influence of the oxidized noble metal material of the measuring electrode which causes the initial offset of the detecting sensitivity of the gas sensor element. To reliably perform the operation for reducing the noble metal material, the oxygen concentration in the treatment atmosphere to which the gas sensor element is exposed in the heat treatment is regulated to be not higher than 0.2%. The oxygen concentration in the treatment atmosphere exceeding 0.2% undesirably lowers the reducing action for reducing the adsorptive gas component at the time of the heat treatment on the gas sensor element, causing a risk that the amount of adsorption of the adsorptive in the adsorptive gas component on the measuring electrode becomes is insufficient. To avoid this, it is needed that the oxygen concentration in the treatment atmosphere is regulated to be not higher than 0.2%.

The lower limit of the oxygen concentration in the treatment atmosphere is not particularly limited, but may be suitably determined to be an appropriately lowered level without a cost increase. For assuring reliable and sufficient reduction of the noble metal material of the measuring electrode and adsorption of the adsorptive in the adsorptive gas component on the measuring electrode by the heat treatment on the gas sensor element in the treatment atmosphere, the oxygen concentration in the treatment atmosphere is preferably held within a range of about $10^{-8}$-0.1%.

As is apparent from the explanation described above, the heat treatment performed on the gas sensor element in the treatment atmosphere according to the present method causes beforehand the adsorption phenomenon of the adsorptive on the measuring electrode and the reduction phenomenon of the noble metal material as the constituent material of the measuring electrode, which phenomena would be caused in the beginning of the measurement of the measurement gas by the gas sensor element which is initially used as the gas sensing device. As a result, the initial deterioration and the initial offset of the measuring sensitivity of the gas sensor element which arise from the phenomena can be avoided, thereby improving the measurement characteristics of the gas sensor element.

Accordingly, the heat treatment of the gas sensor element in the treatment atmosphere is carried out at a temperature in a range from 600° C. to 1000° C. which corresponds to a temperature of the environment in which the gas sensor element is to be used. If the heat treatment is carried out at a temperature lower than 600° C., the adsorption of the adsorptive in the adsorptive gas component, included in the treatment atmosphere, to the measuring electrode and the reduction of the noble metal material constituting the measuring electrode are insufficient, so that the intended improvement in the gas measurement characteristics cannot be attained to a satisfactory extent. Accordingly, the initial offset of the detecting sensitivity to the measurement gas component is not sufficiently prevented or restrained from being caused. If the gas sensor element is subjected to the heat treatment at a temperature exceeding 1000° C., on the other hand, the heat treatment is performed on the gas sensor element at a temperature higher than necessary, activating elimination reaction of the adsorptive from the measuring electrode. Especially, the initial deterioration and the initial offset of the detecting sensitivity of the gas sensor element are not sufficiently eliminated or minimized. In this case, the effect of improvement in the gas measurement characteristics is lowered. Therefore, the temperature at which the heat treatment is performed on the gas sensor element in the treatment atmosphere should be held within the range of 600-1000° C. For further advantageously attaining the improvement in the gas measurement characteristics by performing the heat treatment at the temperature within the range, the heat treatment is performed at a temperature preferably in a range of 750-900° C.

The gas sensor element is subjected to the heat treatment at the temperature described above for time duration of 3-24 hours. Where the gas sensor element is subjected to the heat treatment for short time duration smaller than 3 hours, the improvement in the measurement characteristics of the gas sensor element to be attained by performing the heat treatment is insufficient. On the other hand, where the gas sensor element is subjected to the heat treatment for long time duration exceeding 24 hours, the heat treatment is redundant or lengthy, undesirably deteriorating the efficiency of the heat treatment, accordingly the productivity of the gas sensor element. It is noted that the heat treatment is performed preferably for 4-6 hours.

In the present method, the heat treatment is performed on the gas sensor element in the treatment atmosphere at a temperature of 600-1000° C. for 3-24 hours, preferably at a temperature of 750-900° C. for 4-6 hours. The temperature at which the heat treatment is performed and the time period during which the heat treatment is performed are specifically determined within the respective specified ranges or preferable ranges described above, depending upon the kind and the concentration of the adsorptive gas component included in the treatment atmosphere, for instance.

Thus, in the method according to the invention, the gas sensor element is heated in the treatment atmosphere in which the prescribed amount of the adsorptive gas component and the prescribed amount of the combustible gas are included and in which the oxygen concentration is regulated to a sufficiently low level, at the temperature similar to that of the environment in which the gas sensor element is to be used, for the prescribed time period. By the heat treatment described above, the initial deterioration and the initial offset of the detecting sensitivity to the measurement gas component can be prevented or restrained from being caused. Therefore, the measuring characteristics of the gas sensor element for measuring the measurement gas component can be advantageously improved, so that the measurement of the measurement gas component can be carried out with high accuracy and high stability from the beginning of the measurement using the gas sensor element.

While the preferred embodiment of this invention has been described above for illustrative purpose only, it is to be understood that the present invention may be embodied with various changes and modifications, which may occur to those skilled in the art, without departing from the spirit and scope of the invention.

EXAMPLES

To further clarify the concept of the present invention, some representative examples of the invention will be described. It is to be understood that the invention is not limited to the details of the illustrated examples.

Example 1

Initially, there were prepared seven NOx sensor element specimens each as a gas sensor element having a configuration shown in FIG. 1. Namely, each NOx sensor element specimen includes an electrochemical cell provided by forming, on a solid electrolyte composed of $ZrO_2$, a measuring electrode which is composed of a porous cermet of Rh and $ZrO_2$ and which functions as a catalyst for reducing or decomposing NOx.

Five of the thus prepared seven NOx sensor element specimens were heated in respective heating furnaces for six hours at mutually different temperatures, i.e., 600° C., 700° C., 800° C., 900° C., and 1000° C. In the treatment atmosphere within each heating furnace at the beginning of the heat treatment, the oxygen concentration was regulated to be $10^{-7}$% and $N_2$ was included as a major component. After the initiation of the heat treatment, $N_2$, NO, and $C_3H_6$ were concurrently blown into the treatment atmosphere in each furnace at flow rates of 7.5 L/min, 49 ml/min, and 6 ml/min, respectively, so that the treatment atmosphere in each furnace included NO as the adsorptive gas component in an amount of about 6486 ppm and $C_3H_6$ as the combustible gas in an amount that can be substantially stoichiometrically oxidized by oxygen generated by reduction of NO.

Thus, there were obtained five NOx sensor elements having improved measuring characteristics owing to the heat treatment performed under the conditions specified according to the present invention in the treatment atmosphere which included the adsorptive gas component and the combustible gas in respective amounts within the respective specified ranges and in which the oxygen concentration was regulated to be held within the specified range. The thus obtained five NOx sensors heated at the respective different temperatures of 600° C., 700° C., 800° C., 900° C., and 1000° C. are respectively referred to as invention sensor elements 1 through 5.

One of the two NOx sensor element specimens, which were not subjected to the above-mentioned heat treatment, is referred to as a comparative NOx sensor element 1 whose measuring characteristics are not improved.

The rest (one) of the seven NOx sensor element specimens was heated in a heating furnace at 1100° C. for three hours. The treatment atmospheres in the heating furnace at the beginning and after the initiation of the heat treatment were respectively the same as those used for beginning and after the initiation of the heat treatment of the five NOx sensor element specimens, which were heat treated to prepare the invention sensor elements 1 through 5. In this way, the rest (one) of the seven NOx sensor element specimens was heat treated in a treatment atmosphere in which concentrations of adsorptive gas component, combustible gas, and oxygen were within the ranges of the present invention, respectively. However, the temperature of the heat treatment was higher than that specified in the present invention. Thus obtained NOx sensor element is referred to as a comparative NOx sensor element 2.

Each of the thus obtained unused seven NOx sensor elements (the invention sensor elements 1-5 and the comparative sensor elements 1,2) which are not used yet for measuring the NOx concentration was installed on a portion of an exhaust pipe of an engine having a total displacement of 1800 cc, which portion is located downstream of a portion at which a NOx occluding catalyst is installed, as seen in a flowing direction of an exhaust gas. With each NOx sensor element being installed as described above, the engine was operated according to seven patterns (patterns 1-7) as indicated in the following TABLE 1, such that the seven patterns were repeated in order from the pattern 1 to the pattern 7. Those seven patterns have mutually different numbers of revolution, temperatures of the exhaust gas, and operating times. Thus, life cycle durability evaluation tests were carried out in order to examine chronological changes in the NOx detecting sensitivity of the NOx sensor elements. Deterioration in the NOx detecting sensitivity (hereinafter may be referred to as "NOx detecting sensitivity deterioration") was measured according to a known method for each NOx sensor element at respective time points at which 50 hours, 100 hours, 300 hours, and 500 hours had been respectively elapsed after the initiation of the tests. (Hereinafter, these time points may be respectively referred to as "50-hour time point", "100-hour time point", "300-hour time point", and "500-hour time point".) The deterioration in the NOx detecting sensitivity is represented by a ratio of decrease in the NOx detecting sensitivity at each of the time points with respect to the NOx detecting sensitivity at the moment of initiation of the test (at the moment of initiation of the use of each NOx sensor element). The results are indicated in the graph of FIG. 2 wherein the NOx detecting sensitivity deterioration is represented by negative percentage.

TABLE 1

| Operating pattern | Number of revolution (rpm) | Temperature of exhaust gas (° C.) | Operating time (second) |
|---|---|---|---|
| 1 | 750 | 384 | 225 |
| 2 | 3200 | 483 | 480 |
| 3 | 4500 | 646 | 240 |
| 4 | 750 | 401 | 240 |
| 5 | 2000 | 299 | 480 |
| 6 | 4500 | 622 | 240 |
| 7 | 750 | 454 | 15 |

Figure 2:
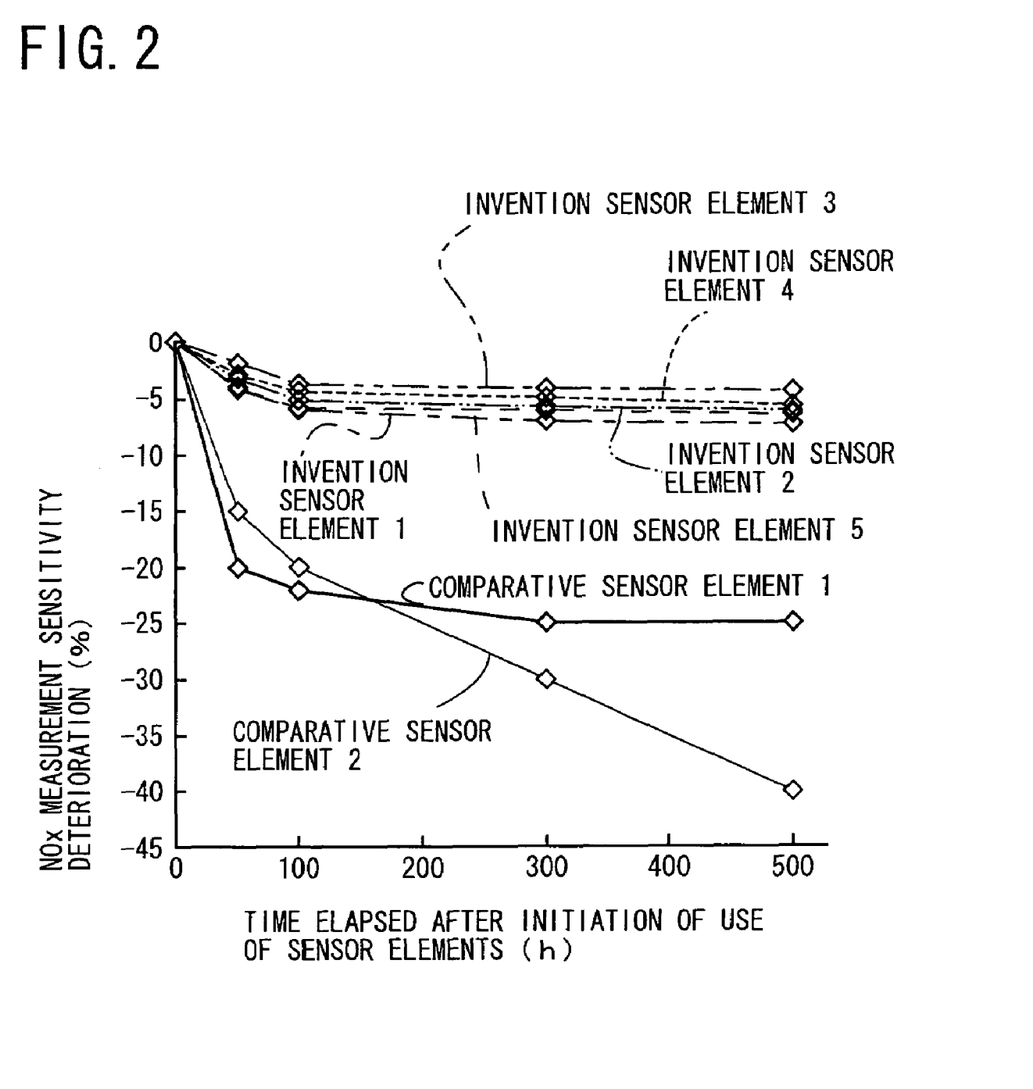
FIG. 2 is a graph showing chronological changes in NOx detecting sensitivity of various NOx sensor elements obtained in EXAMPLE 1.

As is apparent from the graph of FIG. 2, though the invention NOx sensor elements 1-5, which was subjected to the heat treatment for improving the measurement characteristics prior to the use thereof for the measurement of the NOx concentration, suffer from the NOx detecting sensitivity deterioration as extremely small as about −5% in a time period from the moment of initiation of the use to the 100-hour time point, the invention NOx sensor elements 1-5 experience stable NOx detecting sensitivity after the 100-hour time point without substantially any change in the NOx detecting sensitivity. In contrast, the comparative NOx sensor element 1, which was not subjected to the heat treatment according to the present invention for improving the measurement characteristics prior to its use for measuring the NOx concentration, suffers from about −20% of NOx detecting sensitivity deterioration in a time period from the moment of initiation of the use to the 50-hour time point. Further, the NOx detecting sensitivity deterioration in the comparative NOx sensor element 1 is as large as about −25% at the 500-hour time point. The comparative NOx sensor element 2, which was subjected to the heat treatment at a temperature higher than that specified in the present invention prior to the use thereof for the measurement of the NOx concentration, suffers from about −15% of NOx detecting sensitivity deterioration in a time period from the moment of initiation of the use to the 50-hour time point, although the duration of the heat treatment was as short as the lower limit of the range of the duration of the heat treatment of the present invention. Further, the NOx detecting sensitivity deterioration in the comparative NOx sensor element 2 is as large as about −40% at the 500-hour time point. Therefore, it is observed that the comparative NOx sensor element 2 suffers from a more serious NOx detecting sensitivity deterioration than the comparative NOx sensor element, which was not subjected to the heat treatment according to the present invention.

From the results of the tests described above, it is clearly recognized that the initial deterioration in the NOx detecting sensitivity can be effectively prevented by performing the predetermined heat treatment for improving the measurement characteristics according to the present invention on the NOx sensor element prior to its use for measuring the NOx concentration.

Example 2

Initially there were prepared seven NOx sensor element specimens having the same configuration as those used in EXAMPLE 1 indicated above. Five of the seven NOx sensor element specimens were subjected to the heat treatment for improving the measurement characteristics according to the present invention, under the same conditions as those in EXAMPLE 1. Thus, five NOx sensor elements (invention NOx sensor elements 1-5) heated at mutually different temperatures were obtained as in EXAMPLE 1.

One of the two NOx sensor element specimens, which were not subjected to the above-mentioned heat treatment for improving the measurement characteristics was used as a comparative NOx sensor element 1 as in EXAMPLE 1.

The rest (one) of the seven NOx sensor element specimens was heated in a heating furnace at 500° C. for 24 hours. The treatment atmospheres in the heating furnace at the beginning and after the initiation of the heat treatment were respectively the same as those used for beginning and after the initiation of the heat treatment of the five NOx sensor element specimens, which were heat treated to prepare the invention sensor elements 1 through 5. In this way, the rest (one) of the seven NOx sensor element specimens was heat treated in a treatment atmosphere in which concentrations of adsorptive gas component, combustible gas, and oxygen were within the ranges of the present invention, respectively. However, the temperature of the heat treatment was lower than that specified in the present invention. Thus obtained NOx sensor element is referred to as a comparative NOx sensor element 3.

Each of the thus obtained seven NOx sensor elements (the invention sensor elements 1-5 and the comparative sensor elements 1,2) was heated by a heater incorporated therein in an atmosphere without containing NOx until the temperature of each sensor element became 800° C. Further, the voltage for controlling the oxygen concentration in the second internal space including the measurement electrode was controlled to be 450 mV while the voltage for controlling the oxygen concentration in the first internal spaces including the inner pumping electrode was controlled to be 300 mV. In this state, there was measured for each NOx sensor element a pumping current flowing through the electrochemical cell constituted by including the measuring electrode of each NOx sensor element (a pumping current flowing through the measuring pumping cell 36 in the NOx sensor element shown in FIG. 1). Then, the initial offset value of the NOx detecting sensitivity in each NOx sensor element was obtained from the pumping current measured for each NOx sensor element. The results are shown in the graph of FIG. 3.

Figure 3:
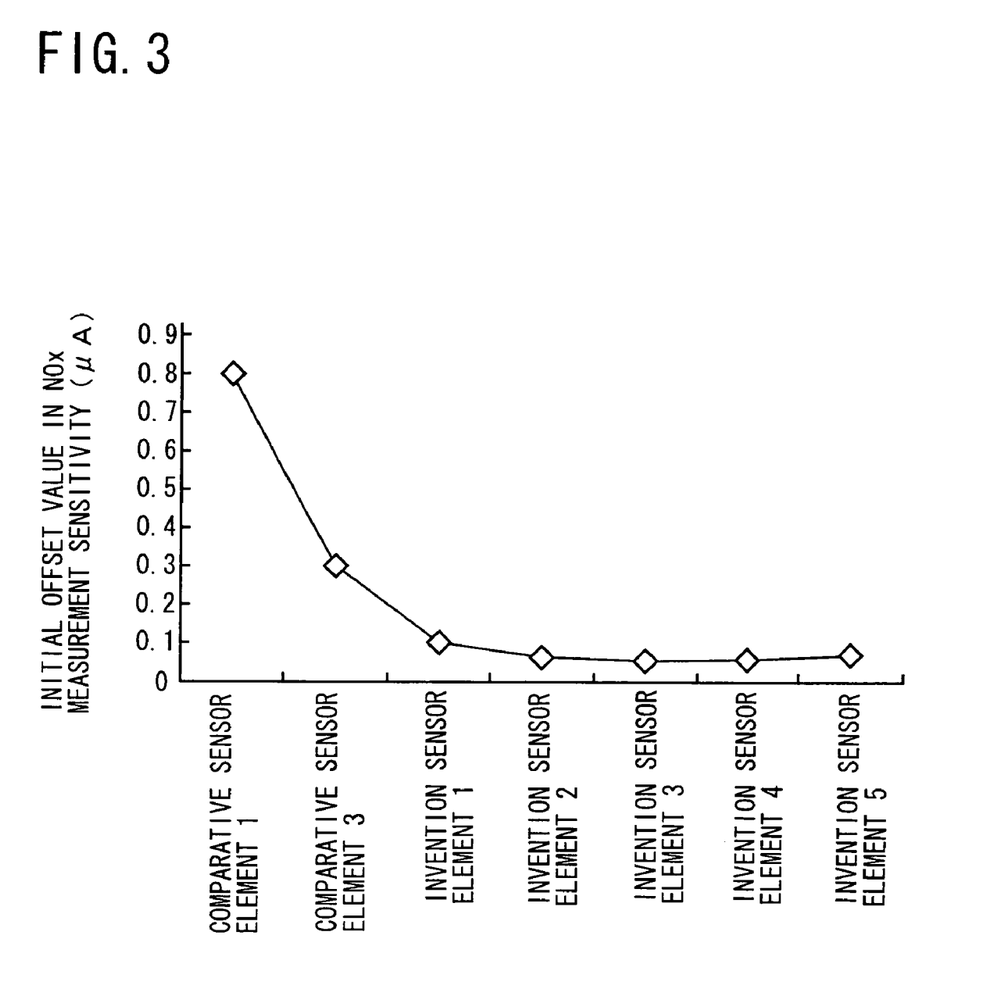
FIG. 3 is a graph showing initial offset values of NOx detecting sensitivity of various NOx sensor elements obtained in EXAMPLE 2.

As is apparent from the graph of FIG. 3, the invention NOx sensor elements 1-5, which were subjected to the heat treatment for improving the measuring characteristics according to the present invention prior to the use thereof for measuring the NOx concentration, have extremely small initial offset values of the NOx detecting sensitivity, i.e., not larger than 0.1 μA. In contrast, the comparative NOx sensor element 1, which was not subjected to the heat treatment for improving the measurement characteristics prior to its use for measuring the NOx concentration, has an extremely large initial offset value of the NOx detecting sensitivity, i.e., about 0.8 μA. The comparative NOx sensor element 3, which was subjected to the heat treatment at a temperature lower than that specified in the present invention prior to the use thereof for the measurement of the NOx concentration, has an initial offset value of the NOx detecting sensitivity of about 0.3 μA, which is apparently larger than that of each of the invention sensor elements 1-5.

The results clearly indicate that the initial offset value of the NOx detecting sensitivity can be sufficiently lowered by performing the predetermined heat treatment for improving the measurement characteristics according to the present invention on the NOx sensor element before it is initially used for measuring the NOx concentration.

What is claimed is:

1. A method of treating a NOx sensor element for improving measurement characteristics thereof, said NOx sensor element including an electrochemical cell provided by forming, on a suitable solid electrolyte, a measuring electrode which is capable of reducing or decomposing a gas component having a bound oxygen in a measurement gas and which is formed of a cermet of a noble metal material and a ceramic material, said NOx sensor element being arranged to reduce or decompose said gas component by said measuring electrode and to measure an amount of oxygen generated upon reduction or decomposition of said gas component, for obtaining a concentration of said gas component in said measurement gas, said method comprising:

heating said NOx sensor element at a temperature of 600-1000° C. for 3-24 hours in a treatment atmosphere in which an oxygen concentration is regulated to be not higher than 0.2% and in which are included: (A) not lower than 1000 ppm of an adsorptive gas component wherein an adsorptive capable of being adsorbed on the measuring electrode is bound to oxygen; and (B) a combustible gas in an amount that can be substantially stoichiometrically oxidized by oxygen that is generated upon reduction or decomposition of said adsorptive gas component, so that said adsorptive gas component is reduced or decomposed for permitting said adsorptive in said adsorptive gas component to be adsorbed on said measuring electrode, and so that said noble metal material of said measuring electrode is reduced.

2. The method according to claim 1, wherein said adsorptive gas component is NO and said NO is included in said treatment atmosphere at a concentration in a range of 3000-7000 ppm.

3. The method according to claim 1, wherein said oxygen concentration in said treatment atmosphere is in a range of $10^{-8}$-0.1%.

4. The method according to claim 1, wherein said heating said NOx sensor element in said treatment atmosphere is carried out at a temperature of 750-900° C. for 4-6 hours.

5. The method according to claim 1, wherein said combustible gas is a hydrocarbon gas.

* * * * *